United States Patent [19]

Kunstle et al.

[11] 4,005,120
[45] Jan. 25, 1977

[54] PROCESS FOR MAKING DIALKOXIBORACETYLACETONATE CONTAINING MIXTURES

[75] Inventors: Gerhard Kunstle, Raitenhaslach; Herbert Siegl, Haiming, both of Germany

[73] Assignee: Wacker-Chemie GmbH, Munich, Germany

[22] Filed: Jan. 7, 1975

[21] Appl. No.: 539,132

[30] Foreign Application Priority Data

Jan. 18, 1974 Germany ............................ 2402426

[52] U.S. Cl. ............................................ 260/462 R
[51] Int. Cl.² ............................................ C07F 5/04
[58] Field of Search .............................. 260/462 R

[56] References Cited

OTHER PUBLICATIONS

Rev. Med. 14(13) 329–330 (1968) Goina et al.

Primary Examiner—Helen M. S. Sneed
Attorney, Agent, or Firm—Allison C. Collard

[57] ABSTRACT

Process for making Dialkoxiboracetylacetonate containing mixtures of the general formula

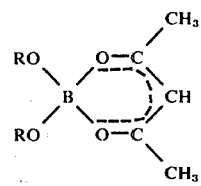

wherein R represents an aliphatic, straight or branched chain, saturated or unsaturated radical with 1–8 carbon atoms, by reacting boric acid trialkyl esters of the general formula $B(OR)_3$ with acetylacetone at temperatures from 10°–150° C, R having the same meaning as above. The mixtures are useful in many synthetic processes, e.g., for catalytic reactions and in the oxidation of hydrocarbons in combustion engines.

5 Claims, No Drawings

PROCESS FOR MAKING DIALKOXIBORACETYLACETONATE CONTAINING MIXTURES

The invention relates to a process for making dialkoxiboracetylacetonate-containing mixtures.

In the art as described in Houben-Weyl 6/2, page 234, bis-acetylacetonates of boron are known, which are ionic complexes, unstable in air, e.g., bis-acetylacetone-boroxonium chloride, produced from boron halides and acetylacetone.

According to the present invention, a process has now been found for making mixtures containing a hitherto unknown dialkoxiboracetylacetonate of the general formula

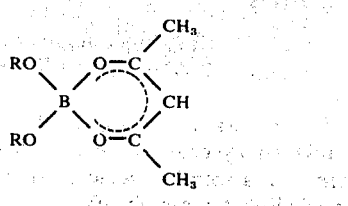

wherein R represents an aliphatic, straight or branched chain, saturated or unsaturated radical with 1–8 carbon atoms, by reacting boric acid trialkyl esters of the general formula $B(OR)_3$ with acetylacetone at temperatures from 10°–150° C, R having the same meaning as above. The dialkoxiboracetylacetonate-containing mixtures according to the invention exhibit considerable stability in air, as compared to the known boron acetylacetonate complexes, and have other favorable properties later discussed.

Examples for aliphatic radicals are methyl, ethyl, n-propyl, isopropyl, allyl, n-butyl, pentyl, hexyl, heptyl, n-octyl or 2-ethylhexyl radicals. The radicals in one molecule of dialkoxiboracetylacetonate may be quite different.

In order to obtain mixtures rich in dialkoxiboracetylacetonate, it is advantageous to work with an excess amount of acetylacetone and to remove by continuous distillation the alcohol formed in the reaction with $B(OR)_3$ — wherein R is an aliphatic radical as defined above, but with 1–4 carbon atoms. It has been proved that it is especially desirable to use acetylacetone in an amount of 200–400% of the theoretical one. Distillation is carried out preferably at reduced pressure and at temperatures ranging from 10°–150° C, more particularly 20°–50° C. The excess amount of acetylacetone is likewise removed by distillation after the reaction is over.

When the boiling point of the alcohol formed is higher than that of acetylacetone, it is desirable to carry on the reaction in the presence of an excess of the latter, up to the point where equilibrium is reached, and to remove by distillation the unreacted starting materials and, if necessary, the alcohol present. In general, these reactions are likewise carried out at temperatures between 10° and 150° C, preferably at 20°–50° C. The dialkoxiboracetylacetonates are products sensitive to temperature and hydrolysis. The splitting increases proportionately with the temperature and leads to the starting and to by-products. It is therefore not possible to isolate dialkoxiboracetylacetonates in pure form. Depending on reaction temperature and time, mixtures are obtained which contain, in addition to the starting materials, boric acid trialkyl ester and acetyl acetone, and/or by-products, such as boric acid, alcohol and condensation products, and 10–99 molar % dialkoxiboracetylacetonate.

The dialkoxiboracetylacetonate obtained according to the invention or the dialkoxiboracetylacetonate containing mixtures, respectively, are, as a rule, readily soluble in organic solvents, such as benzene, toluene, alcohols, chlorinated hydrocarbons, and ethers. Due to their ready solubility and considerable stability in air, as compared to the ionic boron-acetylacetonate complexes known from the literature, the mixtures according to the invention can be used in a number of important starting, intermediate, and end products where they exhibit their characteristic effectiveness. They are useful, for instance, in catalytic processes and in the oxidation of hydrocarbons in combustion engines.

The process of the invention will be more fully described in a number of examples, which are given by way of illustration and not of limitation.

EXAMPLE 1

DIMETHOXIBORACETYLACETONATE 26 grams boric acid trimethylester and 50 grams acetylacetone are mixed and the mixture is distilled at 1 torr, without exceeding the temperature of 30° C.

The distillation residue obtained amounts to 12 grams of a crystalline mash which according to KMR-spectrum consists of 75 molar % dimethoxiboracetylacetonate and 25 molar % boric acid trimethyl ester.

EXAMPLE 2

DIALLYLOXIBORACETYLACETONATE 91 grams boric acid triallyl ester and 100 grams acetylacetone are mixed and the mixture is distilled at 0.05 torr without exceeding the temperature of 40° C.

The distillation residue amounts to 47.5 grams of a very mobile brown-yellow liquid, which according to KMR-spectrum consists of 93 molar % diallyloxiboracetylacetonate and 7 molar % boric acid triallyl ester.

EXAMPLE 3

DI-n-PROPOXIBORACETYLACETONATE 94 grams boric acid tri-n-propyl ester and 100 grams acetylacetone are mixed and the mixture is distilled at 0.1 torr without exceeding a temperature of 30° C.

The distillation residue obtained amounts to 31 grams of a very mobile yellow liquid, which consists according to KMR-spectrum of 85 molar % di-n-propoxiboracetonate and 15 molar % boric acid tri-n-propyl ester.

EXAMPLE 4

DI-BUTOXIBORACETYLACETONATE 115 grams boric acid tri-butyl ester and 100 grams acetylacetone are mixed and the mixture is distilled at 0.05 torr without exceeding a temperature of 55° C. The distillation residue obtained amounts to 14 grams of a light yellow oil, which according to KMR-spectrum consists of 95 molar % of di-butoxiboracetylacetonate and 5 molar % of boric acid tri-butyl ester.

EXAMPLE 5

120 parts by weight of acetylacetone and 10 parts by weight of boric acid tri-butyl ester are first introduced into a stirring vessel and heated to boiling at 100 torr. While stirring, another 36 parts by weight of the ester are added drop by drop depending on the amount of pure butanol escaping over an efficiently operating column connected to the stirring vessel. In this operation care should be taken that by appropriate fractionation (reflux separation), the escaping butanol is as free as possible of acetylacetone. During this reaction, the temperature in the stirring vessel should not exceed 85° C. At the same temperature, the unreacted starting products are subsequently removed over the column by continued increase of the vacuum to 1 torr.

The residue obtained in the stirring vessel amounts to 55 parts by weight of a dark red-brown liquid, which according to KMR-spectrum contains, in addition to 45 molar % of di-butoxiboracetylacetonate, some boric acid tri-butyl ester and acetylacetone or various by-products of the ester and the acetylacetone.

EXAMPLE 6

Boric acid tri-2-ethylhexyl ester is heated with the double amount of its weight with acetylacetone to 125° C for 4 hours. Thereupon, the unreacted acetylacetone, the 2-ethylhexanol formed, and finally the unreacted boric acid tri-ethylhexyl ester are removed by distillation from the reaction mixture, at first at a slight vacuum, then at 0.05 torr, the temperature not exceeding 125° C.

The obtained residue contains in addition to di-2-ethylhexoxiboracetylacetonate mainly boric acid tri-2-ethylhexyl ester, acetylacetone and undefined by-products or split products.

It will be obvious to those skilled in the art that other changes and variations can be made in carrying out the present invention without departing from the spirit and scope thereof as defined in the appended claims.

What is claimed is:

1. A process for making mixtures containing dialkoxiboracetylacetonate of the general formula

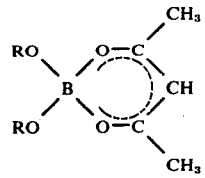

wherein R represents a member selected from the group consisting of aliphatic straight chain and branched chain, saturated and unsaturated hydrocarbon group with 1–8 carbon atoms, the process consisting of reacting boric acid trialkyl esters of the general formula $B(OR)_3$, wherein R has the meaning defined above, with acetylacetone at temperatures ranging from 10°–150° C while removing ROH alcohol formed in the reaction by continuous distillation at reduced pressure.

2. The process according to claim 1, wherein the boric acid trialkyl ester of the formula $B(OR)_3$, wherein R represents a member selected from the group consisting of aliphatic straight chain and branched chain, saturated and unsaturated hydrocarbon group with 1 – 4 carbon atoms, is reacted with acetylacetone.

3. The process according to claim 1, wherein the reaction is carried out at a temperature of 20°–50° C.

4. The process according to claim 1, wherein the reaction is carried out with an excess amount of acetylacetone.

5. The process according to claim 1, the dialkoxiboracetylacetonate-containing mixtures prepared contain 10–99 molar % of dialkoxiboracetylacetonate and in addition thereto boric acid trialkyl ester, acetylacetone and their by-products and split products.

* * * * *